United States Patent
Ambeck-Madsen et al.

(10) Patent No.: US 11,612,343 B2
(45) Date of Patent: Mar. 28, 2023

(54) METHOD AND SYSTEM FOR DETERMINING THE INTENTION OF A USER OF A VEHICLE TO BRAKE OR ACCELERATE

(71) Applicants: TOYOTA MOTOR EUROPE, Brussels (BE); CAMLIN ITALY S.R.L, Parma (IT)

(72) Inventors: Jonas Ambeck-Madsen, Brussels (BE); Ichiro Sakata, Brussels (BE); Luca Ascari, Parma (IT); Giovanni Vecchiato, Parma (IT); Maria Del Vecchio, Parma (IT); Fabio Deon, Parma (IT); Pietro Avanzini, Parma (IT); Giacomo Rizzolatti, Parma (IT)

(73) Assignees: TOYOTA MOTOR EUROPE, Brussels (BE); CAMLIN ITALY S.R.L., Parma (IT)

( * ) Notice: Subject to any disclaimer, the term of this patent is extended or adjusted under 35 U.S.C. 154(b) by 526 days.

(21) Appl. No.: 16/635,789

(22) PCT Filed: Aug. 4, 2017

(86) PCT No.: PCT/EP2017/069863
§ 371 (c)(1),
(2) Date: Jan. 31, 2020

(87) PCT Pub. No.: WO2019/025016
PCT Pub. Date: Feb. 7, 2019

(65) Prior Publication Data
US 2021/0077005 A1    Mar. 18, 2021

(51) Int. Cl.
*A61B 5/18* (2006.01)
*G06N 20/00* (2019.01)
(Continued)

(52) U.S. Cl.
CPC ............... *A61B 5/18* (2013.01); *A61B 5/316* (2021.01); *A61B 5/374* (2021.01); *B60W 40/09* (2013.01);
(Continued)

(58) Field of Classification Search
CPC ........... A61B 5/18; A61B 5/374; A61B 5/316; G06N 20/00; G06N 5/04; B60W 40/09; B60W 50/0097; B60W 2540/22
See application file for complete search history.

(56) References Cited

U.S. PATENT DOCUMENTS

| 6,175,762 B1 * | 1/2001 | Kirkup | ................... A61B 5/375 600/544 |
| 6,928,354 B2 * | 8/2005 | Ryu | ....................... B60K 28/06 280/28.11 |

(Continued)

FOREIGN PATENT DOCUMENTS

| KR | 10-1632830 B1 | 6/2016 |
| WO | 2014/092494 A1 | 6/2014 |

OTHER PUBLICATIONS

Il-Hwa Kim et al., "Detection of braking intention in diverse situations during simulated driving based on EEG feature combination", Journal of Neural Engineering, 2015, pp. 1-12, vol. 12. (Year: 2015).*

(Continued)

*Primary Examiner* — Ramsey Refai
(74) *Attorney, Agent, or Firm* — Sughrue Mion, PLLC (57) ABSTRACT

A method for determining the intention of a user of a vehicle to brake or accelerate, comprising:
acquiring (100) a plurality of EEG signals on the user,
applying (101) a predetermined spatial filter on the plurality of EEG signals so as to obtain a target EEG component,
detecting (102) a spectral pattern in the EEG component corresponding to an intention to brake or detecting a phase pattern in the EEG component corresponding to an intention to accelerate.

17 Claims, 5 Drawing Sheets

(51) Int. Cl.
  *A61B 5/374*   (2021.01)
  *A61B 5/316*   (2021.01)
  *B60W 40/09*   (2012.01)
  *B60W 50/00*   (2006.01)
  *G06N 5/04*    (2023.01)

(52) U.S. Cl.
  CPC ........... *B60W 50/0097* (2013.01); *G06N 5/04* (2013.01); *G06N 20/00* (2019.01); *B60W 2540/22* (2013.01)

(56) References Cited

U.S. PATENT DOCUMENTS

| | | | |
|---|---|---|---|
| 10,463,271 B2* | 11/2019 | Intrator | A61B 5/369 |
| 2004/0117098 A1 | 6/2004 | Ryu et al. | |
| 2007/0010754 A1* | 1/2007 | Muller | G05B 13/027 |
| | | | 180/272 |
| 2010/0191140 A1* | 7/2010 | Terada | A61B 5/6814 |
| | | | 600/544 |
| 2015/0338917 A1* | 11/2015 | Steiner | H04L 9/3271 |
| | | | 345/156 |
| 2016/0167672 A1* | 6/2016 | Krueger | G16H 40/63 |
| | | | 340/576 |
| 2016/0287124 A1* | 10/2016 | He | A61B 5/291 |

OTHER PUBLICATIONS

Zahra Khaliliardali et al., "Action prediction based on anticipatory brain potentials during simulated driving", Journal of Neural Engineering, 2015, pp. 1-12, vol. 12, No. 6.
Andreea Loana Sburlea et al., "Advantages of EEG phase patterns for the detection of gait intention in healthy and stroke subjects", Journal of Neural Engineering, 2017, pp. 1-15, vol. 14, No. 3.
International Search Report of PCT/EP2017/069863 dated Mar. 29, 2018 [PCT/ISA/210].
Written Opinion of PCT/EP2017/069863 dated Mar. 29, 2018 [PCT/ISA/237].

* cited by examiner

METHOD AND SYSTEM FOR DETERMINING THE INTENTION OF A USER OF A VEHICLE TO BRAKE OR ACCELERATE

CROSS REFERENCE TO RELATED APPLICATIONS

This application is a National Stage of International Application No. PCT/EP2017/069863, filed Aug. 4, 2017.

FIELD OF THE DISCLOSURE

The present disclosure is related to the determination of a driving intention of a user in a vehicle using electroencephalography (EEG) signals.

DESCRIPTION OF RELATED ART

Brain Computer Interfaces (BCI) can be used as interface between a human and an object to be controlled by the brain of a user. Typically, in a Brain Computer Interface, EEG signals are acquired to determine the intention of the user by analyzing the EEG signals.

There have been solutions disclosed in which EEG signals are acquired and inputted to a software component, for example in the field of motor imagery, in which the software learns the brain patterns of the user associated with repeated motor thoughts.

Document US 20070010754 discloses a method in which cerebral current signals of a vehicle occupant are acquired. These signals are then used to determine the intention of the occupant in real time. This document does not provide enough details on how to implement its Brain Controlled Interface.

Document US 2004117098 discloses a Brain Computer Interface which acquires a feature using a single electrode at a certain frequency to detect the intention of a driver to act on the brakes so as to start braking before the driver presses the brake pedal. The solution of this document is not robust enough, and only one action can be determined.

Document JP2001030886 discloses a method to detect an intention of braking of a user based on EEG signals. This method is limited to detecting an intention of braking.

Document "Detection of braking intention in diverse situations during simulated driving based on EEG feature combination" (Kim et al, 2015: Kim, I.-H., Kim, J.-W., Haufe, S., Lee, S.-W., 2015. J. Neural Eng. 12, 016001. doi:10.1088/1741-2560/12/1/016001) discloses a method to identify soft braking (a type of braking not caused by external constraints) on the basis of features of the EEG signals. This method is limited to the detection of braking events.

None of these documents allow discriminating an intention to brake from an intention to accelerate, namely two actions undertaken with the same limb.

It is a primary object of the disclosure to provide methods and system that overcome the deficiencies of the currently available systems and methods.

SUMMARY OF THE DISCLOSURE

The present disclosure overcomes one or more deficiencies of the prior art by proposing a method for determining the intention of a user of a vehicle (for example the driver of a vehicle such as an automobile) to brake or accelerate, comprising:

acquiring a plurality of EEG signals on the user,
applying a predetermined spatial filter on the plurality of EEG signals so as to obtain a target EEG component,
detecting a spectral pattern (for example a predetermined pattern or a learned pattern obtained by machine learning) in the EEG component corresponding to an intention to brake or detecting a spectral pattern (for example a predetermined pattern or a learned pattern obtained by machine learning) in the EEG component corresponding to an intention to accelerate.

An intention to brake can therefore be determined before the user actually performs the actions required for braking the vehicle (typically using the right foot to press the brake pedal), or if the user intends to accelerate, and intention to accelerate can therefore be determined before the user actually performs the actions required for accelerating (typically using the right foot to press the accelerator pedal).

The inventors of the present invention have observed that it is possible to obtain a component of the EEG signals through spatial filtering on which it is possible to discriminate a braking intention from an accelerating intention. Thus, with respect to the methods of the prior art, the above-method allows also detecting an intention to accelerate.

EEG signals are usually acquired using a plurality of electrodes placed on the head of the user. Each electrode may be placed at a predefined location, for example using the 10-20 system well known to the person skilled in the art. A spatial filter takes these locations into account so as to produce a component which appears to be placed at a target location. This component can be obtained through a linear combination of the EEG signals (an example of such methods being the Independent Component Analysis, or ICA).

The parameters of the spatial filter can be determined through tests and calibrations to obtain a component on which it is possible to detect different patterns for braking and accelerating. Also, the spectral patterns can be determined through tests and calibrations. In these tests and calibrations, EEG signals are recorded while a user drives (and more precisely brakes and accelerates).

It should be noted that the above method can be performed in real-time (i.e. not on a recorded signal but while the signal is being acquired). For example, the steps of the method can be performed before the user actually brakes or accelerate. For example, the steps of the method can be performed in a duration which is less than approximately 1.3 second (it has been observed that the frequency patterns appear around 1.3 second before the braking or accelerating actually occurs).

According to a particular embodiment, the method comprises determining the instantaneous power of the EEG component according to frequency and time, and wherein detecting said spectral patterns comprises detecting a spectral pattern (for example a predetermined pattern or a learned pattern obtained by machine learning) in the instantaneous power of the EEG component within a predetermined spectral saliency mask (or map, the two terms being equivalent) corresponding to an intention to brake or detecting a spectral pattern (for example a predetermined pattern or a learned pattern obtained by machine learning) in the instantaneous power of the EEG component within the predetermined spectral saliency mask corresponding to an intention to accelerate.

According to a particular embodiment, the predetermined spatial filter is centered in the vicinity of the Fz and Cz locations in the 10-20 EEG system.

The inventors of the present disclosure have observed that said component is centered in the vicinity of the Fz and Cz locations.

By centered, it is meant that the receptive field of the filter (i.e. the area of cortex the filter extract information from) is in vicinity of the Fz and Cz locations.

The electrodes used to obtain the component could therefore be placed in the positions corresponding to the highest and lowest coefficients of the spatial filter.

According to a particular embodiment, the EEG signals are acquired at the Cz, P3, O2, Fz, F4, and C5 locations in the 10-20 EEG system.

For example, the EEG signals can be acquired at only these 6 locations using six electrodes. Alternatively, only 3, 4 or 5 of these locations could be used to obtain the EEG signals. The person skilled in the art will be able to determine how many electrodes are needed to obtain the component in view of the spatial filter, taking into account the application. These locations are sufficient to obtain said component and a good determination of an intention to brake or an intention to accelerate.

According to a particular embodiment, detecting said spectral patterns is performed in a frequency band comprising at least the $\alpha$ and $\theta$ frequency bands.

The $\alpha$ and $\theta$ frequency bands are frequency bands of EEG signals well known to the skilled person which respectively correspond to 8 to 12 Hertz and to 4 to 8 Hertz.

The inventors of the present disclosure have observed that spectral patterns, for example Event Related Spectral Perturbation (ERSP, known to the skilled person) which allow discrimination between intention to brake and intention to accelerate are generally in these frequency bands.

According to an embodiment, the method further comprises an additional detection of a phase pattern in the EEG component or in the EEG signals corresponding to an intention to brake or an additional detection of a phase pattern in the EEG component or in the EEG signals corresponding to an intention to accelerate.

Thus, it is proposed to use two different features of the EEG component or of the EEG signals, one relating to shifts in the power spectrum (called spectral pattern) and another one relating to shifts in the instant signal phase (called phase pattern). The additional detection increases the robustness of the method because the determination of the intention of the user can be based on the two features.

For example, determining the intention of a user of a vehicle to brake or accelerate can be based on the detection of one of the spectral patterns and one of the phase patterns.

Figure 4:
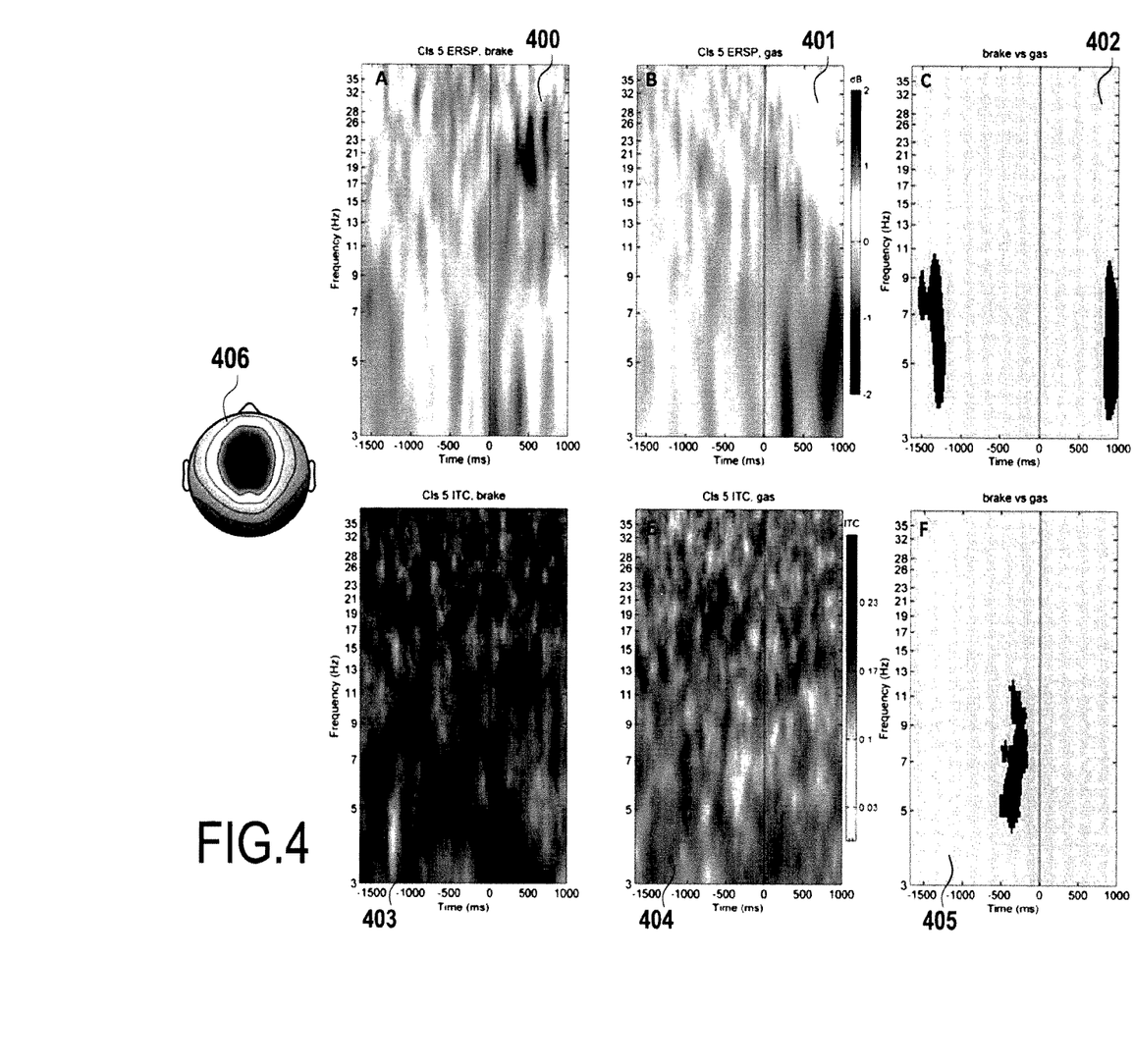
FIG. 4 shows different spectral and phase representations.

The use of phase patterns results from inventors of the present disclosure having also observed an increased Intertrial coherence (known as ITC, computed in an offline analysis, for example during calibration) in the brake epochs with respect to acceleration epochs within a certain spectral saliency mask (a region with a specific frequency occupancy, time localization and time duration); this indicates an instant-phase distribution peaked around a given value in the $[-\pi; \pi]$ interval. The proximity of the instant phase to such value, evaluated within the statistical significance (saliency) masks in FIG. 405, can be used for the real-time detection of the phase feature called phase pattern.

According to an embodiment, detecting said spectral pattern is performed at a first instant in the EEG component and detecting said phase patterns is performed at a second instant in the EEG component or in the EEG signals, the first instant and the second instant being separated by a first predetermined duration.

It has been observed by the inventors of the present disclosure that the spectral patterns which allow discrimination between accelerating and braking can be detected at a first instant which is typically between 1.5 and 1.3 seconds before the actual action occurs (when the pedal starts to be pressed). It has also been observed that the phase patterns which allow discrimination between accelerating and braking can be detected at a second instant which is typically between 0.5 and 0.3 second before the actual action occurs.

For example, the predetermined first duration is comprised between 0.8 and 1.2 seconds.

According to a particular embodiment, the method comprises storing a time window of the EEG component having at least a predetermined second duration.

This time window can be stored in a circular buffer, or a delay line, or a memory block, so as to update this time window with every new sample of the EEG component. Using the time window facilitates the detection of the phase patterns.

According to a particular embodiment, the method comprises:
detecting an intention to move the right foot of the user using the EEG signals at a third instant,
if an intention to move the right foot of the user is detected, performing said detection of the spectral patterns at the first instant in the stored time window of the EEG component, the first instant and the third instant being separated by said predetermined second duration.

It has been observed by the inventors of the present disclosure that by detecting an intention to move a right foot (which typically occurs 0.3 second before the actual action occurs, when the pedal starts to be pressed), it is possible to know precisely where to detect the spectral patterns in the stored window. Thus, this increases the robustness of the method.

The person skilled in the art knows how to detect an intention to move a right foot. For example, document US20040117098 discloses a method which could be used to detect an intention to move a right foot of the user. Document "Action prediction based on anticipatory brain potentials during simulated driving" (Khaliliardali, Z., Chavarriaga, R., Gheorghe, L.A., Millán, J. del R., 2015. J. Neural Eng. 12, 066006. doi:10.1088/1741-2560/12/6/066006) discloses a method to determine such an intention.

According to a particular embodiment, the predetermined second duration is comprised between 0.2 and 1.2 seconds.

According to a particular embodiment, detecting said phase patterns is performed at the second instant in the stored time window of the EEG component.

According to a particular embodiment, said phase patterns comprise a phase realignment.

According to a particular embodiment, detecting a phase realignment comprises:
extracting the Hilbert transform from the EEG signal or signal component, so as to obtain instantaneous phase shifts,
extracting the first derivative from the instantaneous phase shifts, so as to obtain the phase realignment.

According to a particular embodiment, detecting said phase realignment comprises:
extracting the wavelet decomposition of the EEG signal or the EEG signal component,
assessing, within a predetermined phase saliency map (for example extracted in a calibration phase), whether the instantaneous phase approaches (for example when the value reaches a predefined threshold) predetermined or learned phase values (for example the values of the instant phase observed during calibration in an epoch corresponding to a braking event or to an acceleration event).

According to a particular embodiment, detecting said phase patterns comprises:

generating a plurality of sinusoidal signals having predetermined frequencies for example within a predefined phase saliency map and a phase set at said third instant, calculating a cross correlation between the signals of the plurality of sinusoidal signals and stored time window of the EEG component at said second instant in the stored time window of the EEG component.

According to a particular embodiment, detecting a spectral pattern is performed using a machine-learning classifier and/or detecting a phase pattern is performed using a machine-learning classifier.

According to a second aspect, the disclosure also provides a system for determining the intention of a user of a vehicle to brake or accelerate, comprising:

an acquisition module of a plurality of EEG signals on a user in the vehicle, a processor, a memory comprising instructions executable by the processor to:

acquire a plurality of EEG signals on the user, apply a predetermined spatial filter on the plurality of EEG signals so as to obtain a target EEG component, detect a spectral pattern in the EEG component corresponding to an intention to brake or detecting a spectral pattern in the EEG component corresponding to an intention to accelerate.

perform a soft classification process based on the plurality of preliminary soft predictions so as do obtain the driving intention of the user.

This system can be configured to carry out all the embodiments of the method for determining a driving intention of a user of a vehicle as described above.

In one particular embodiment, the steps of the method for determining a driving intention of a user of a vehicle are determined by computer program instructions.

Consequently, the invention is also directed to a computer program for executing the steps of a method as described above when this program is executed by a computer.

This program can use any programming language and take the form of source code, object code or a code intermediate between source code and object code, such as a partially compiled form, or any other desirable form.

The invention is also directed to a computer-readable information medium containing instructions of a computer program as described above.

The information medium can be any entity or device capable of storing the program. For example, the medium can include storage means such as a ROM, for example a CD ROM or a microelectronic circuit ROM, or magnetic storage means, for example a diskette (floppy disk) or a hard disk.

Alternatively, the information medium can be an integrated circuit in which the program is incorporated, the circuit being adapted to execute the method in question or to be used in its execution.

BRIEF DESCRIPTION OF THE DRAWINGS

How the present disclosure may be put into effect will now be described by way of example with reference to the appended drawings, in which.

DESCRIPTION OF THE EMBODIMENTS

An exemplary method and system for determining a driving intention will be described hereinafter.

Figure 1:
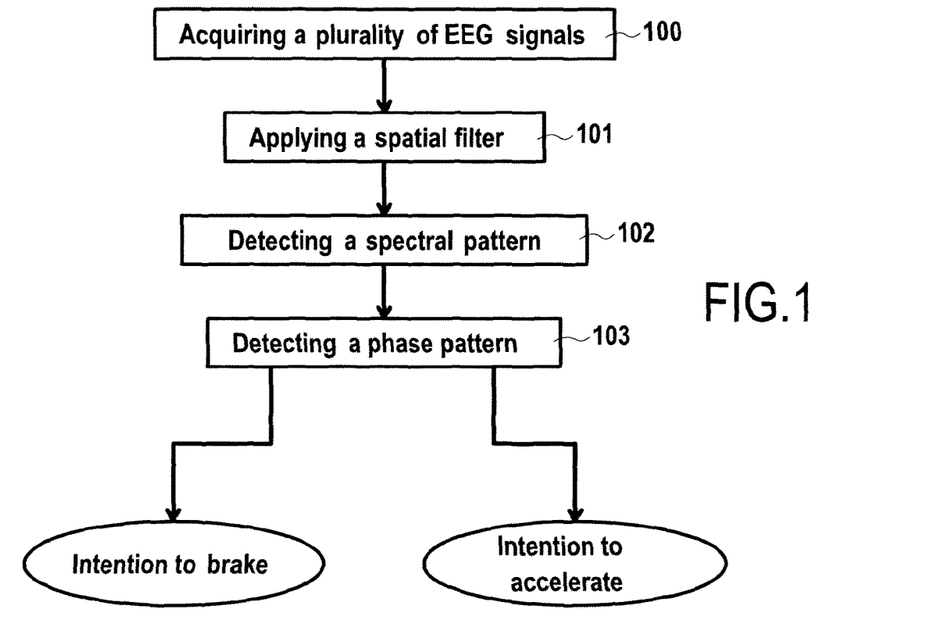
FIG. 1 is a block diagram of an exemplary method for determining a driving intention of a user of a vehicle using EEG signals.

A method for determining a driving intention of a user of a vehicle using electroencephalography (EEG) signals is represented on FIG. 1.

EEG signals can be acquired (step 100 on FIG. 1) in a traditional manner by placing a plurality of electrodes on the head of a user to obtain signals illustrating the electrical activity of the brain of the user. These EEG signals can be obtained while the user is in a vehicle, for example an automobile (or a wheelchair, a pod, an exoskeleton, or a remote artifact or robotic system which can be driven to brake/accelerate, or one or more artificial limbs which can also be driven to brake/accelerate, etc.), and more precisely while the user is able to drive the vehicle (for example while the user is in the vehicle or, if the vehicle can be remotely controlled, while the user is using a remote control interface of the vehicle).

The EEG signals can be acquired using the arrangement known to the skilled person as a 10-20 system.

Alternatively, only a subset of electrodes from the 10-20 system can be used to acquire the EEG signals. For example, only the Cz, P3, O2, Fz, F4, and C5 locations in the 10-20 EEG system can be used, because it has been observed that acquiring signals at only these locations is sufficient to discriminate an intention to brake from an intention to accelerate.

It should be noted that the acquired EEG signals of FIG. 1 can be referred to as EEG channels by the person skilled in the art.

In a second step 101, a spatial filter is applied to the EEG signals. This spatial filter is centered in the vicinity of the Fz and Cz locations in the 10-20 EEG system.

In a third step 102, a predetermined spectral pattern (in this example, the spectral pattern is predetermined; alternatively, it can be learned by machine learning) in the EEG component corresponding to an intention to brake or a predetermined spectral pattern in the EEG component corresponding to an intention to accelerate are detected.

Step 102 can be performed by determining the instantaneous power of the EEG component according to the frequency, and by detecting a predetermined spectral pattern in the instantaneous power of the EEG component within a predetermined spectral saliency map corresponding to an intention to brake or detecting a predetermined spectral pattern in the instantaneous power of the EEG component within the predetermined spectral saliency map corresponding to an intention to accelerate.

If none of these patterns is detected, then it is considered that no braking or accelerating intention is detected in the EEG signals acquired by the user.

While it is possible to only use the detection of spectral patterns to determine whether the user intends to brake or to accelerate, a better detection is obtained by using a further detection so as to confirm the result of step 102.

Thus, if one of the spectral patterns is detected, step 103 is carried out in which a predetermined phase pattern (in this example, the phase pattern is predetermined; alternatively, it can be learned by machine learning) in the EEG component (the invention is not limited to determining the phase pattern in the EEG component, the EEG signals may also be used to this end in specific embodiments) within a phase saliency map corresponding to an intention to brake or an additional detection of a predetermined phase pattern in the EEG component within a phase saliency map corresponding to an intention to accelerate.

Through tests and calibrations, it is possible to determine that specific phase patterns which allow discrimination between braking and accelerating can be detected at a certain instant after the detection of one of the spectral patterns.

In other words, detecting said spectral pattern is performed at a first instant in the EEG signal and detecting said phase patterns is performed at a second instant in the EEG signal, the first instant and the second instant being separated by a first predetermined duration.

The predetermined first duration is comprised between 0.8 to 1.2 second.

The detection of a phase pattern can be performed on a stored time window of the EEG component, and it can consist in determining phase resets (or phase realignments).

The phase patterns can be detected in real time by searching for phase resets within the phase saliency map. It is possible to use the Hilbert transform to identify a phase resetting (or phase realignment). Using the Hilbert transform, a plurality of time series of instantaneous phase differences is computed and the first derivative of the time series of the phase differences is extracted. Peaks in the time series indicate phase shifts, and intervals having a small derivative indicate phase locks, which are the components of the phase resets that are being looked for.

Alternatively, the detection of patterns in the instant signal phase can rely on the wavelet decomposition of the EEG signal or component: the instant signal phase, with respect to the predicted foot movement onset, can be estimated by wavelet decomposition, using e.g. Morlet wavelets. The increased ITC (obtained during offline analysis/calibration) in brake epochs (the phase pattern visible in the below described FIG. 4 and which bears reference 403) indicates an instant-phase distribution peaked around a given value in the [−π; π] interval (peak more pronounced than in the distribution for acceleration epochs). The proximity to such value of the instant phase, evaluated within the phase saliency map (the statistical significance masks in the below described FIG. 4 and which bears reference 405), can be used for the real-time detection of the phase feature.

Alternatively, a phase reset can be highlighted by generating a plurality of sinusoidal signals having predetermined frequencies within and without the phase saliency map (for example at 4, 6, 7 and 9 Hertz) phase locked to a specific time instant (for example the instant when the spectral patterns are detected), and by calculating a cross correlation between the signals of the plurality of sinusoidal signals and stored time window of the EEG component at said second instant in the stored time window of the EEG component.

A decrease in the cross correlation indicates this phase realignment. The co-occurrence of phase resets within the phase saliency map can be used as feature to distinguish brake from acceleration intention.

It should be noted that the detection of the spectral and phase patterns can be carried out in the $\alpha$ and $\theta$ frequency bands (for example, a preliminary band-pass filter can be used).

It should be noted that the detection of the spectral and phase patterns can be carried out within spectral and phase saliency maps, defining frequency ranges (including the $\alpha$ and $\theta$ bands), durations, time boundaries.

It should also be noted that observing a variation in cross-correlation between sinusoidal components is only a possible solution to detect the phase patterns. Alternatively, it is possible to use autoregressive-moving-average (ARMA) models so as to generate a synthetic component of the EEG component in the $\alpha$ and $\theta$ frequency bands and to check for phase shifts with the real signals within the phase saliency map.

It is also possible to measure cross-frequency phase shifts at the instant when the phase pattern should be detected. For example, cross-frequency phase locking and cross-frequency phase shift can be measured by the second derivative of instantaneous cross-frequency phase differences which is equal to 0 when there is phase locking and is strictly superior to zero when there is a cross-frequency phase shift.

Afterwards it is possible to determine an intention to brake or an intention to accelerate. If none of the phase patterns is detected then it is considered that no braking or accelerating intention is detected in the EEG signals acquired by the user.

The steps of the methods described in reference to FIG. 1 can be determined by computer instructions. These instructions can be executed on a processor of a system, as represented on FIG. 2.

Figure 2:
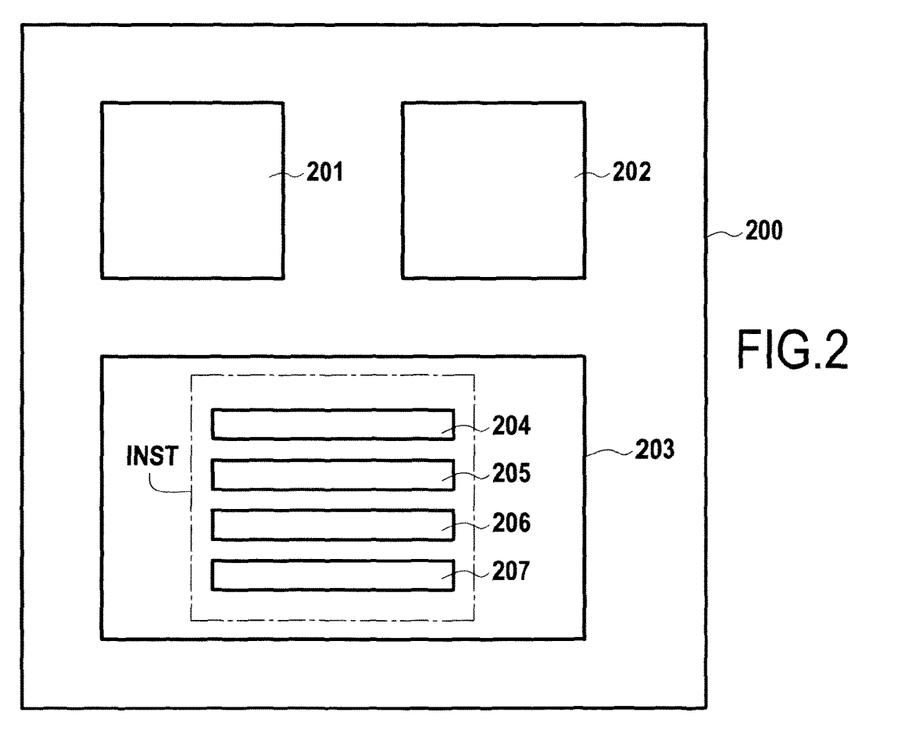
FIG. 2 is a schematic diagram of a system for determining a driving intention of a user of a vehicle using EEG signals

On this figure, a system 200 has been represented. This system comprises a processor 201, an acquisition module 202 of a plurality of EEG signals on a user in the vehicle, and a memory 203.

This acquisition module 202 can comprise a connection interface with the electrodes which may be connected to the user. It may also comprise amplification modules so as to obtain the EEG signals.

The memory 203 can be a non-volatile memory and it comprises a set of instructions (or computer program) INST which can be executed by the processor 201 to perform the method described in reference to FIG. 1. The set of instructions INST comprises:
- a first instruction 204 to acquire a plurality of EEG signals on the user,
- a second instruction 205 to apply a predetermined spatial filter on the plurality of EEG signals so as to obtain a target EEG component,
- a third instruction 206 to detect a predetermined spectral pattern in the EEG component corresponding to an intention to brake or detecting a predetermined spectral pattern in the EEG component corresponding to an intention to accelerate, and
- a fourth instruction 207 to detect a predetermined phase pattern in the EEG component corresponding to an intention to brake or detecting a predetermined phase pattern in the EEG component corresponding to an intention to accelerate.

Figure 3:
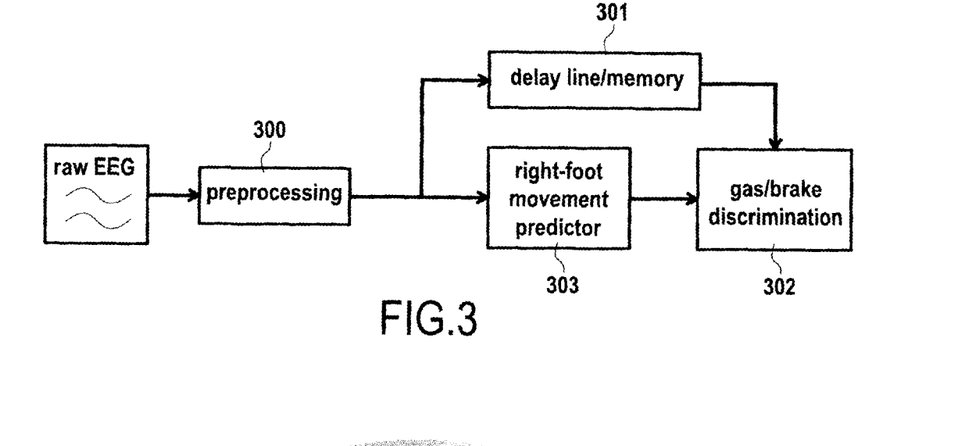
FIG. 3 is a block diagram of the steps of an exemplary method in which a delay line/memory block is used.

FIG. 3 is a block diagram of the steps of an exemplary method in which a delay line/memory block is used to store a time window of the EEG component described in reference to FIG. 1.

In a first step 300, the raw EEG signals obtained on a user are preprocessed. This step can comprise the application of a spatial filter (step 101 of FIG. 1) and other types of filtering can be applied. For example, it is possible to use a band pass filter to obtain a component which is limited to the α and θ frequency bands.

The skilled person will know which additional treatments can be applied to the signals or to the EEG component in the preprocessing step 300.

The EEG component is then stored in a delay line or memory block 301, which can consist in a circular buffer which will be updated with every new sample.

Step 301 is configured to provide a time window of the EEG component having a duration which allows detecting the spectral patterns as well as the phase patterns in the same time window.

These detection are performed in step 302 in which the patterns are detected.

In order to make the detection more accurate, an intention to move the right foot of the user is detected in step 303 using the EEG component (it should be noted that detecting a movement of a right foot can also be performed on the EEG signals, for example using additional frequency bands such as the β band). Various methods known by the person skilled in the art can be used to detect an intention to move a right foot.

It has been observed by the inventors of the present disclosure that by detecting an intention to move a right foot (which typically occurs 0.3 second before the actual action occurs, when the pedal starts to be pressed), it is possible to know precisely where to detect the frequency patterns and the phase patterns in the stored window. In fact, during tests and calibration phases, it has been observed that the spectral patterns appear 1.3 second before the actual action occurs and that the phase patterns appear 0.3 second before the actual action occurs. Thus, the time window has to be able to store at least one second of signal so as to allow going back to the time when the frequency pattern can be detected.

Also, when detecting the phase patterns using a plurality of generated sinusoidal signals, it is possible to set the phase of the generated signals at the time of the detection of an intention to move a right foot.

On FIG. 4 different graphical representations of the spectral power and intertrial coherence (phase-related) have been represented for braking epochs (time windows) for accelerating epochs, and for statistical comparisons between the two.

More precisely, the data used to obtain the graphical representations of FIG. 4 are obtained during calibration and testing phases, i.e. before performing the steps of the method as described in reference to FIG. 1 or 3.

Representation 400 corresponds to the Event Related Spectral Perturbation (ERSP). ERSP is a two dimensional (frequency by latency) image of mean change in spectral power from baseline. In other words, they are event-related variations in the power spectrum (its amplitude at certain frequencies). The skilled person knows how to obtain the representation 400.

On representation 400, the time value zero corresponds to a braking event, and more precisely to the onset of action on the pedal (starting of the pedal movement).

Representation 401 also corresponds to an ERSP but the event of this representation is an acceleration the onset of action on the pedal (starting of the pedal movement).

Representation 402 is the statistical significance mask, also called spectral saliency map, in the comparison between the braking and accelerating events. The p-value is set at 0.05 so as to show that the ERSP for braking and the ERSP for accelerating have differences which are statistically significant and not random.

As can be seen on representation 402, a significant pattern can be observed 1.3 seconds before the actual action starts. This representation has been obtained after a plurality of calibrations and tests have been performed on a plurality of users. Thus, the spectral patterns at 1.3 seconds before the actual action allow discriminating between braking and accelerating, and these patterns can be used on a plurality of user without requiring specific adaptations.

Representation 403 corresponds to the Intertrial coherence (ITC). ITC is a two dimensional (frequency by latency) image of the strength of phase locking of the EEG signals to a time-locking event. The skilled person knows how to obtain representation 403.

On representation 403, the time value zero corresponds to a braking event, and more precisely to the onset of action on the pedal (starting of the pedal movement).

Representation 404 also corresponds to an ITC but the event of this representation is an acceleration the onset of action on the pedal (starting of the pedal movement).

Representation 405 is the statistical significance mask, also called phase saliency map, in the comparison between the braking and accelerating events. As can be seen on this representation, a significant pattern can be observed 0.3 seconds before the actual action starts. This representation has been obtained after a plurality of calibrations and tests have been performed on a plurality of users. Thus, the phase patterns at 0.3 seconds before the actual action allow discriminating between braking and accelerating, and these patterns can be used on a plurality of user without requiring specific adaptations.

Representation 406 is the spatial filter which can be used to obtain the EEG component. as can be seen on the representation, the spatial filter is centred in the vicinity of the Fz and Cz electrode locations (the image contribution is darker in this area).

Figure 5:
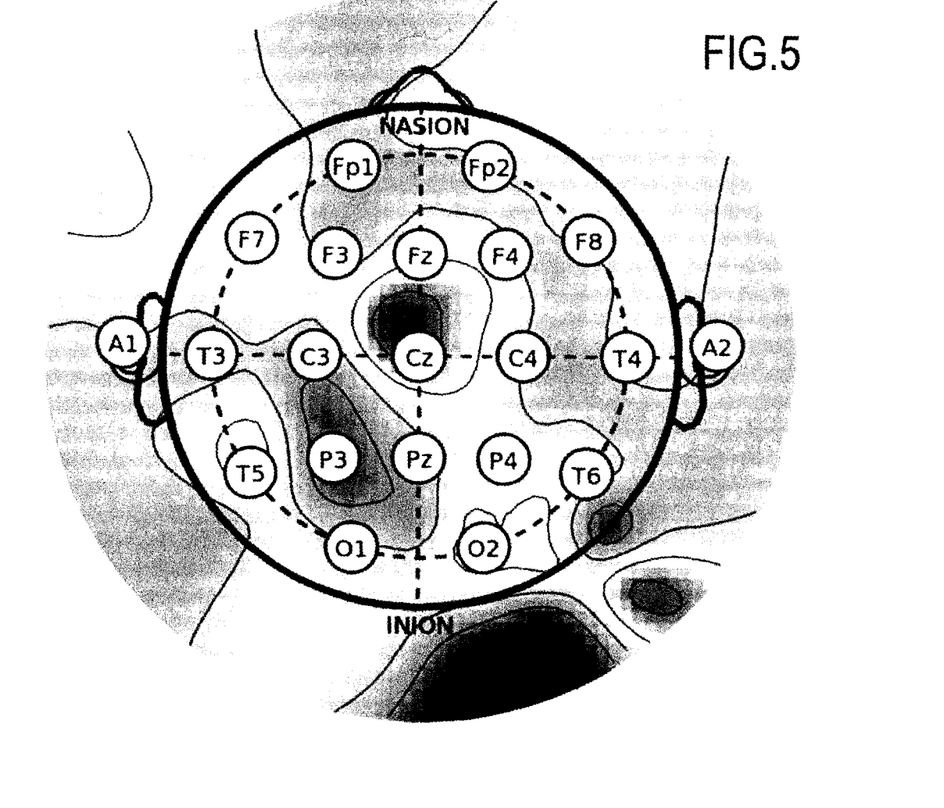
FIG. 5 is representation of the contribution of the electrodes in the spatial filter.

FIG. 5 is a representation of the 10-20 system superimposed with the contributions of the electrodes in the spatial filter. Darker areas indicate a high contribution from the electrodes covering the areas.

Figure 6:
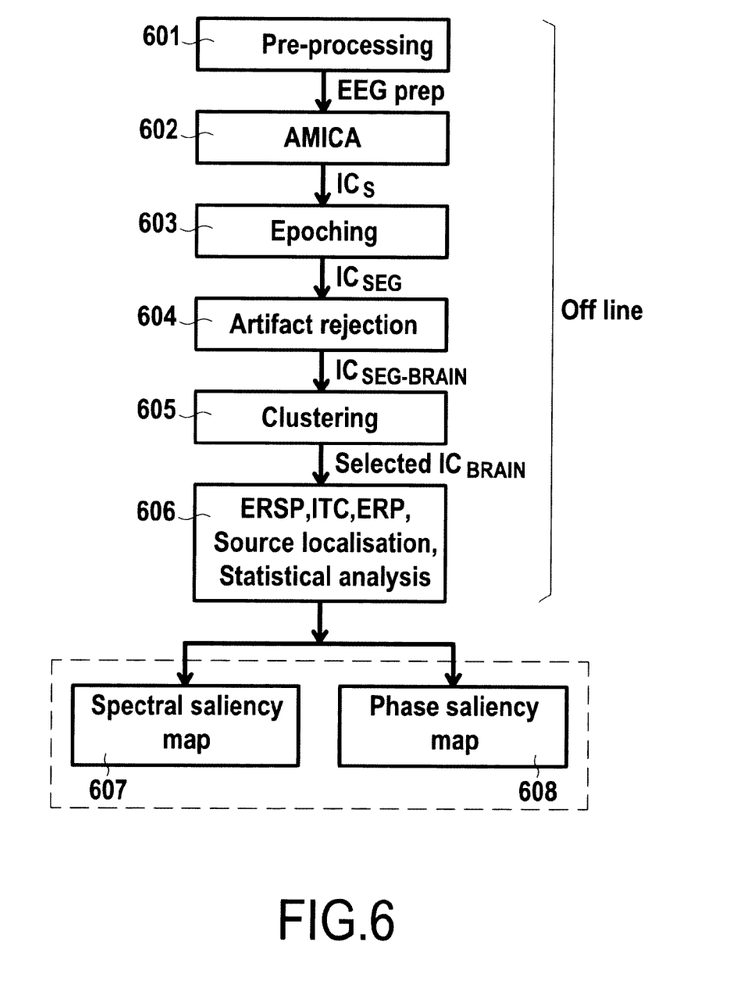
FIG. 6 is a block diagram of the steps for obtaining spectral and phase saliency maps.

FIG. 6 is a block diagram of the steps carried out to obtain the spectral patterns, the phase patterns, and the saliency maps. The steps of FIG. 6 allow obtaining the graphical representations of FIGS. 4 and 5.

In a first step 601, continuous EEG recordings are down sampled at 250 Hz and pre-processed by means of the PREP pipeline (for example disclosed by Bigdely-Shamlo, N., Mullen, T., Kothe, C., Su, K.-M., Robbins, K. A., 2015, in "The PREP pipeline: standardized preprocessing for large-scale EEG analysis". Front. Neuroinformatics 9. doi: 10.3389/fninf.2015.00016) with the aim of removing line noise at 50 and 100 Hz, interpolating bad channels and referencing the dataset to a common average.

In a second step 602, the Adaptive Mixture Independent Component Analysis (AMICA, Delorme et al., 2012; Palmer et al., 2011) is performed on the EEG principal components explaining or covering 99% of data variance.

In a third step 603, the EEG data obtained after step 602 were segmented in time windows ranging between [−2000, 1000] ms, and locked on the onset of the pedal pressure. This process is usually referred to by the person skilled in the art as "epoching".

In a fourth step 604, artefacts are rejected by applying an automatic procedure to detect abnormal trends and abnormal spectra). In order to identify and separate neurophysiological brain activities from the artefactual ones, the equivalent dipole source localization (known to the skilled person under the acronym DIPFIT2) is performed and the independent components (ICs) are automatically separated by means of the SASICA plugin (Chaumon et al., 2015 (for example as disclosed by Chaumon, M., Bishop, D. V. M., Busch, N. A., 2015., in "A practical guide to the selection of independent components of the electroencephalogram for artifact correction". J. Neurosci. Methods, Cutting-edge EEG Methods 250, 47-63. doi:10.1016/j.jneumeth.2015.02.025). Default parameters were used for the autocorrelation, focal components, focal trial activity, and ADJUST routines. Channels E126, E127 were used to capture blinks with the FASTER routine, while the dipole fit residual variance threshold was set at 0.15. A total of 192 ICs were then inspected by topography and spectra to further discard remaining artefactual activations.

In a fifth step 605, 122 ICs are used for a following cluster analysis performed to group them according to their scalp topographies via the k-means algorithm. The dimension of the cluster space was set to 109, which is the minimum number of good EEG channels remaining across participants after pre-processing. The correlation distance measure was chosen to compute centroid clusters. The number of clusters to compute can be chosen by adopting a bootstrap-based method, through a measure called the Stability Index (SI) (for example as disclosed by Ben-Hur, A., Elisseeff, A., Guyon, I., 2002. In "A stability based method for discovering structure in clustered data". Pac. Symp. Biocomput. Pac. Symp. Biocomput. 6-17). The SI is a measure of the similarity computed by partitioning two randomly selected sub-sets from the original dataset. The SI is estimated for values of k between 2 and 20, and the number of clusters in the dataset can be determined by comparing it to a distribution of SI values calculated from a surrogate dataset with no cluster structure. The number k exceeding the 95th percentile of the null distribution with the highest value of SI was selected as cluster number.

A final step 606 is then carried out in which, for each cluster, the event-related spectral perturbation (ERSP, event-related shifts in the power spectrum) and the inter-trial coherence (ITC, even related phase locking) are computed (for example as disclosed by Makeig, S., Debener, S., Onton, J., Delorme, A., 2004. In "Mining event-related brain dynamics" Trends Cogn. Sci. 8, 204-210. doi:10.1016/j.tics.2004.03.008). The time frequency decomposition was obtained by using Morlet wavelets whose frequency increased from 3 to 125 Hz in 100 logarithmically spaced steps. Similarly, the number of wavelet cycles increased from 3 to 25 in logarithmic steps. A conversion to dB is performed taking the pre-event interval [−1800, 0] ms as baseline. The choice of such baseline increased the robustness of the analysis since the pre-movement activity is normalized according to the average value of the same activity. In such a way, it is assured that any other choice of baseline (i.e., [−1800, 1000] or [0, 1000] ms) would only enhanced already existing differences. Vice versa, using a baseline comprising post event interval would highlight differences which could not belong to the only pre-movement interval.

The obtained brake and gas time frequency patterns are then compared by means of dependent samples t-statistic relying on nonparametric permutation testing, corrected for multiple comparisons using the weighted cluster mass correction with a number of randomization of 1000 and a statistical threshold of 0.05 (for example as disclosed by Hayasaka, S., Nichols, T. E., 2004. In "Combining voxel intensity and cluster extent with permutation test framework" NeuroImage 23, 54-63. doi:10.1016/j.neuroimage.2004.04.035).

The above described steps 601 to 606 allow obtaining the spatial filter for which the contributions of the electrodes are shown on FIG. 5, and the graphical representations of FIG. 4. Most notably, the spectral saliency map 607 is obtained and the phase saliency map 608 is obtained.

It is in these saliency maps that spectral and phase patterns can be detected. These patterns can be determined in a calibration step.

Figure 7:
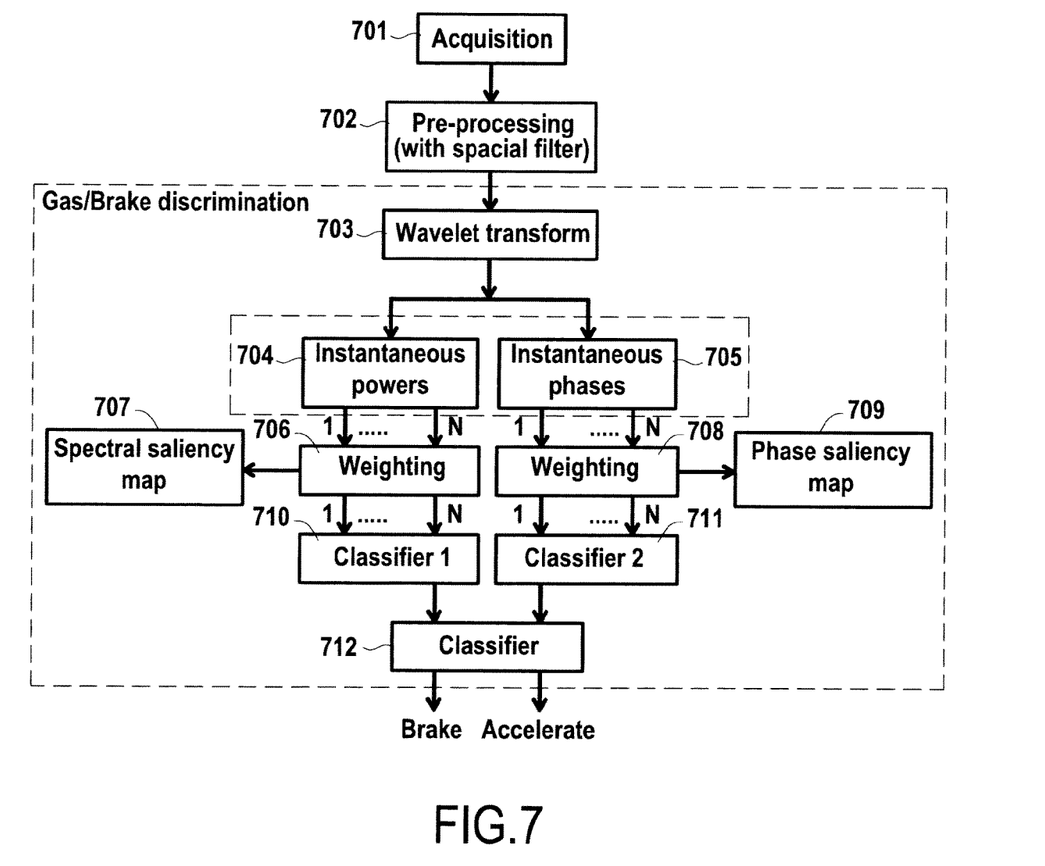
FIG. 7 is a block diagram of the steps for on-line processing the EEG signals to identify the spectral and phase patterns corresponding to the intention to brake or to accelerate

FIG. 7 is a block diagram of the steps for on-line processing the EEG signals to identify the spectral and phase patterns corresponding to the intention to brake or to accelerate In step 701, EEG signals are acquired on a user driving a vehicle.

In step 702, a spatial filter is applied to the EEG signals (for example the filter 406 of FIG. 4) to obtain an EEG component.

The following steps are performed to detect the presence of spectral and phase patterns in the EEG component.

In step 703, a wavelet transform is applied to the EEG component.

Then, the instantaneous powers and phases are extracted for N frequencies of the EEG component respectively in steps 704 and 705.

The N instantaneous powers are weighed (step 706) using a predetermined spectral saliency map 707. The N instantaneous phases are weighed (step 708) using a predetermined spectral saliency map 709.

Then, two machine-learning classifiers 710 and 711 to provide preliminary driving intentions (for example neural networks or other classifiers known from the field of machine learning) are used to determine the presence of phase and spectral patterns, potentially learned by the same machine learning classifiers during the off line test and calibration phase. Thus, in this example, the phase and spectral patterns are learned.

An additional machine-learning classifier 712 (for example a neural network or another classifier known from the field of machine learning) is used so as to deliver the final driving intention between braking and accelerating.

The invention claimed is:

1. A method for determining the intention of a user of a vehicle to brake or accelerate, comprising:
    acquiring a plurality of EEG signals on the user,
    applying a predetermined spatial filter on the plurality of EEG signals so as to obtain a target EEG component,
    detecting a spectral pattern in the EEG component corresponding to an intention to brake or detecting a spectral pattern in the EEG component corresponding to an intention to accelerate, and
    detecting (i) a phase pattern in the EEG component or in the EEG signals corresponding to an intention to brake or (ii) a phase pattern in the EEG component or in the EEG signals corresponding to an intention to accelerate, wherein said phase patterns comprise a phase realignment,
    wherein detecting said phase patterns comprises:
    generating a plurality of sinusoidal signals having predetermined frequencies and a phase set at a third instant, and
    calculating a cross correlation between the signals of the plurality of sinusoidal signals and a stored time window of the EEG component at a second instant in the stored time window of the EEG component.

2. The method according to claim 1, comprising determining an instantaneous power of the EEG component according to frequency and time, and wherein detecting said spectral patterns comprises detecting a spectral pattern in the instantaneous power of the EEG component within a predetermined spectral saliency mask corresponding to an intention to brake or detecting a spectral pattern in the instantaneous power of the EEG component within the predetermined spectral saliency mask corresponding to an intention to accelerate.

3. The method according to claim 1, wherein the predetermined spatial filter is centered in a vicinity of Fz and Cz locations in a 10-20 EEG system.

4. The method according to claim 1, wherein the EEG signals are acquired at Cz, P3, O2, Fz, F4, and C5 locations in a 10-20 EEG system.

5. The method of claim 1, wherein detecting said spectral patterns is performed in a frequency band comprising at least the $\alpha$ and $\theta$ frequency bands.

6. The method of claim 1, wherein detecting said spectral pattern is performed at a first instant in the EEG component and detecting said phase patterns is performed at the second instant in the EEG signals or in the EEG component, the first instant and the second instant being separated by a first predetermined duration.

7. The method of claim 6, wherein the predetermined first duration is comprised between 0.8 and 1.2 seconds.

8. The method according to claim 1, comprising
storing the time window of the EEG component having at least a predetermined second duration.

9. The method according to claim 8, comprising:
detecting an intention to move the right foot of the user using the EEG signals at the third instant,
if an intention to move the right foot of the user is detected, performing said detection of the spectral patterns at the first instant in the stored time window of the EEG component, the first instant and the third instant being separated by said predetermined second duration.

10. The method according to claim 8, wherein the predetermined second duration is comprised between 0.2 and 1.2 seconds.

11. The method according to claim 8, further comprising an additional detection of a phase pattern in the EEG component or in the EEG signals corresponding to an intention to brake or an additional detection of a phase pattern in the EEG component or in the EEG signals corresponding to an intention to accelerate, and wherein detecting said phase patterns is performed at the second instant in the stored time window of the EEG component.

12. The method according to claim 1, wherein detecting a phase realignment comprises: extracting a Hilbert transformation from the EEG signals or the EEG component so as to obtain instantaneous phase shifts, extracting a first derivative from the instantaneous phase shifts, so as to obtain the phase realignment.

13. The method according to claim 1, wherein detecting a phase realignment comprises: extracting a wavelet decomposition of the EEG signals or of the EEG component, assessing, within a predetermined phase saliency map, whether the instantaneous phase approaches predetermined or learned phase values.

14. The method of claim 1, wherein detecting a spectral pattern is performed using a machine-learning classifier and/or wherein detecting a phase pattern is performed using a machine-learning classifier.

15. A system for determining the intention of a user of a vehicle to brake or accelerate, comprising:
an acquisition module of a plurality of EEG signals on a user in the vehicle,
a processor,
a memory comprising instructions (INST) executable by the processor to:
acquire a plurality of EEG signals on the user,
apply a predetermined spatial filter on the plurality of EEG signals so as to obtain a target EEG component,
detect a spectral pattern in the EEG component corresponding to an intention to brake or detecting a spectral pattern in the EEG component corresponding to an intention to accelerate, and
detect (i) a phase pattern in the EEG component or in the EEG signals corresponding to an intention to brake or (ii) a phase pattern in the EEG component or in the EEG signals corresponding to an intention to accelerate, wherein said phase patterns comprise a phase realignment,
wherein the detection of said phase patterns comprises:
generating a plurality of sinusoidal signals having predetermined frequencies and a phase set at a third instant, and
calculating a cross correlation between the signals of the plurality of sinusoidal signals and a stored time window of the EEG component at a second instant in the stored time window of the EEG component.

16. An electronic control unit comprising a processor and a memory that includes a program including instructions for executing the steps of a method according to claim 1 when said program is executed by the processor.

17. A non-transitory recording medium readable by a computer and having recorded thereon a computer program including instructions for executing the steps of a method according to claim 1.

* * * * *